(12) United States Patent
Joly et al.

(10) Patent No.: US 10,467,764 B2
(45) Date of Patent: Nov. 5, 2019

(54) METHOD FOR COUNTING AND CHARACTERIZATION OF PARTICLES IN A FLUID IN MOVEMENT

(71) Applicant: Commissariat a l'energie atomique et aux energies alternatives, Paris (FR)

(72) Inventors: Pierre Joly, Grenoble (FR); Rodrigue Rousier, Bournainville (FR); David Elvira, Igny (FR)

(73) Assignee: Commissariat A L'Energie Atomique et aux Energies Alternatives, Paris (FR)

( * ) Notice: Subject to any disclaimer, the term of this patent is extended or adjusted under 35 U.S.C. 154(b) by 0 days.

(21) Appl. No.: 15/856,679

(22) Filed: Dec. 28, 2017

(65) Prior Publication Data

US 2018/0189963 A1 Jul. 5, 2018

(30) Foreign Application Priority Data

Dec. 28, 2016 (FR) ...................................... 16 63475

(51) Int. Cl.
*G06T 7/246* (2017.01)
*G03H 1/04* (2006.01)
(Continued)

(52) U.S. Cl.
CPC ......... *G06T 7/248* (2017.01); *G01N 15/1429* (2013.01); *G01N 15/1434* (2013.01);
(Continued)

(58) Field of Classification Search
CPC ........... G06T 7/248; G06T 2207/10152; G06T 2207/20224; G01N 15/1429;
(Continued)

(56) References Cited

U.S. PATENT DOCUMENTS

| 2008/0306386 A1* | 12/2008 | Baba | .................. | A61B 8/06 |
| | | | | 600/455 |
| 2010/0110177 A1* | 5/2010 | Yamada | ............. | G01N 15/1463 |
| | | | | 348/135 |

(Continued)

FOREIGN PATENT DOCUMENTS

| FR | 3 031 180 | 7/2016 |
| WO | WO 2008/090330 A1 | 7/2008 |

OTHER PUBLICATIONS

French Preliminary Search Report dated Nov. 1, 2017 in French Application 16 63475 filed Dec. 28, 2016 (with English Translation of Categories of Cited Documents and Written Opinion).

(Continued)

*Primary Examiner* — Huy T Nguyen
(74) *Attorney, Agent, or Firm* — Oblon, McClelland, Maier & Neustadt, L.L.P.

(57) ABSTRACT

A method allowing particles to be tracked in a moving fluid, via an optical method. The particles are in motion in a fluidic chamber. An image of the fluidic chamber is acquired, so as to obtain three-dimensional positions of particles in the fluidic chamber at a first time. Three-dimensional positions of 10 particles at a second time are also obtained, the second time being subsequent to the first time. On the basis of the obtained three-dimensional positions, potential movements of particles, between said times, are established. On the basis of a model of movement of the particles, potential movements are validated. The validated movements allow the particles in the fluid to be counted. In addition, if 15 the particles are of different nature, the movement model may comprise a component of movement of the particles with respect to the fluid that is characteristic of this difference. Determining this component then allows the particles to be characterized.

19 Claims, 6 Drawing Sheets

(51) Int. Cl.
*G01N 15/14* (2006.01)
*H04N 5/225* (2006.01)
*G01N 15/10* (2006.01)
*G03H 1/00* (2006.01)

(52) U.S. Cl.
CPC ....... *G01N 15/1459* (2013.01); *G03H 1/0443* (2013.01); *H04N 5/2256* (2013.01); *G01N 2015/1006* (2013.01); *G01N 2015/144* (2013.01); *G01N 2015/1454* (2013.01); *G01N 2015/1486* (2013.01); *G03H 2001/0033* (2013.01); *G03H 2001/0447* (2013.01); *G03H 2210/62* (2013.01); *G06T 2207/10152* (2013.01); *G06T 2207/20224* (2013.01)

(58) Field of Classification Search
CPC ........... G01N 15/1434; G01N 15/1459; G01N 2015/1006; G01N 2015/144; G01N 2015/1454; G01N 2015/1486; G03H 1/0443; G03H 2001/0033; G03H 2001/0447; G03H 2210/62; H04N 5/2256
See application file for complete search history.

(56) References Cited

U.S. PATENT DOCUMENTS

| | | | |
|---|---|---|---|
| 2011/0136165 A1* | 6/2011 | Vojnovic | G01N 15/1456 435/39 |
| 2013/0107261 A1* | 5/2013 | Duplisea | G01N 21/27 356/404 |
| 2016/0153959 A1 | 6/2016 | Vojnovic et al. | |

OTHER PUBLICATIONS

Pasquale Memmolo, et al., "Twin-beams digital holography for 3D tracking and quantitative phase-contrast microscopy in microfluidics," Optics Express vol. 19 No. 25, 2011, pp. 25833-25842.

* cited by examiner

METHOD FOR COUNTING AND CHARACTERIZATION OF PARTICLES IN A FLUID IN MOVEMENT

TECHNICAL FIELD

The technical field of the invention is the counting of particles flowing through a fluidic chamber using an optical method.

PRIOR ART

Several optical methods have already been employed to count particles circulating in a fluid, the fluid being a gas or a liquid. A very widespread technique is based on the illumination, using a light beam, of a fluid in which particles are flowing. When a particle passes through the beam, some of the light is scattered and may be detected by a photodetector. This technique has been employed to detect particles in air, or to detect cells in liquids, biological liquids for example.

Other methods are based on the analysis of images, for example using a microscope, but such images provide only two-dimensional information as regards the position of the particles.

Document WO2008090330 describes a device allowing samples including cells to be observed via lensless imaging. The sample is placed between a light source and an image sensor, without placing an image-forming optical system between the sample and the image sensor. Thus, the image sensor collects an image, also called a hologram, formed from the interference patterns of interference between the light wave emitted by the light source and transmitted by the sample, and diffracted waves resulting from diffraction, by the sample, of the light wave emitted by the light source. These interference patterns are generally made up of a succession of concentric rings. They are sometimes referred to as diffraction patterns. In this way, images the field of observation of which is clearly larger than that of a microscope are obtained. When the concentration of cells in the sample is sufficiently low, one interference pattern may be associated with each cell; counting them allows the cells present in the sample to be counted. However, holograms do not allow cells to be reliably counted when concentration increases and/or when the particles are moving. This method also reaches its limits when the hologram has a low signal-to-noise ratio, for example when the size of a particle is small or when a particle has a refractive index close to that of the medium forming the sample.

Patent application US2012/148141 describes a method, based on the same principles as WO2008090330, implementing a holographic reconstruction algorithm that is applied to a succession of acquired images in order to reconstruct complex images of spermatozoa. The objective is to characterize their motility. It is a method based on tracking the individual paths of mobile particles, in an immobile fluid, on the basis of three-dimensional particle coordinates obtained by holographic reconstruction. Specifically, such a reconstruction allows a distance between an image sensor and a particle to be estimated, allowing what is called depth information to be determined, this information complementing two-dimensional information obtained with conventional image sensors. Moreover, the method allows a movement model to be determined for each particle, the movement model being a result obtained by implementing the method.

Moreover, many particle imaging velocimetry (PIV) flow imaging methods implement optical methods for detecting particles so as to characterize their movement, which is representative of the movement of the studied fluid.

The inventors of the present invention have proposed a method allowing particles flowing through a fluidic chamber to be located and counted, this method being automatable, and implementable on a moving fluid. The method may be implemented automatically, and used to address high quantities of particles or high speeds. In addition, when particles of various types are present in the fluidic chamber, the method may allow various types of particles to be discriminated and hence the number of particles of various types to be counted, on the basis of their respective movements.

SUMMARY OF THE INVENTION

One subject of the invention is a method for counting particles moving in a fluid, flowing through a fluidic chamber, the method including the following steps:

a) placing the fluidic chamber between a light source and an image sensor, the image sensor lying in a detection plane;

b) illuminating the fluidic chamber with the light source, the light source emitting an incident light wave that propagates along a propagation axis, and acquiring, with the image sensor, an image, called the first image, representative of a light wave, called the exposure wave, to which the image sensor is exposed, the image sensor including various pixels, each pixel being associated with a radial coordinate in the detection plane;

c) on the basis of the acquired image, obtaining coordinates, in particular three-dimensional coordinates, of particles, in the fluidic chamber, at a first time;

d) obtaining coordinates, in particular three-dimensional coordinates, of particles in the fluidic chamber at a second time, subsequent to the first time;

e) on the basis of the coordinates of the particles obtained at the first time and at the second time, determining potential movements of the particles between said times;

f) taking into account a model of the movement of the fluid in the fluidic chamber;

g) on the basis of the model of the movement of the fluid considered in step f), validating movements among the potential movements calculated in step e); and h) on the basis of the movements validated in step g), determining a number of particles and/or coordinates of the particles at the first time and/or at the second time.

Steps f) and g) are optional. When they are not implemented, the method includes a step of determining a number of particles and/or coordinates of the particles at the first time and/or at the second time on the basis of the potential movements determined in step e).

Step c) may include:

obtaining a first image of interest from the first image acquired in step b) and applying a digital propagation operator to the first image of interest in order to propagate it, by at least one reconstruction distance, along the propagation axis, so as to obtain at least one reconstructed complex image; and on the basis of each reconstructed complex image, obtaining radial coordinates of particles in the fluidic chamber at the first time.

Step c) may include the following substeps:

ci) obtaining a first image of interest from the first image acquired in step b), and applying a digital propagation operator to the first image of interest in order to propagate it, by a plurality of reconstruction distances, along the propagation axis, so as to obtain a first stack of reconstructed complex images, called the first stack of images, including as many reconstructed complex images as there are reconstruction distances, each reconstructed complex image being representative of an exposure light wave to which the image sensor is exposed;

cii) for at least one radial coordinate defined by the first image of interest, determining a reconstruction distance that maximizes the variation in a component of each complex image forming the first stack of images, along an axis parallel to the propagation axis and passing through said radial coordinate, said determined reconstruction distance forming a transverse coordinate associated with said radial coordinate, the value of the component calculated at said reconstruction distance being what is called a maximum value associated with said radial coordinate, substep cii) being carried out for all or some radial coordinates associated with the pixels of the first image of interest;

ciii) establishing a list of three-dimensional positions, each three-dimensional position including a radial coordinate and the associated transverse coordinate determined in substep cii), each three-dimensional position being associated with the maximum value obtained in substep cii); and civ) selecting three-dimensional positions depending on the maximum value that is associated therewith.

The first image of interest may be:

the first image acquired in step b);

or the first image acquired in step b), from which is subtracted an image of the fluidic chamber, acquired by the image sensor, prior or subsequently to the acquisition of the first image, the subtraction being weighted by a weighting term, the weighting term possibly being a real number comprised between 0 and 1;

or the first image acquired in step b), from which is subtracted an average of images acquired prior and subsequently to the acquisition of the first image, respectively.

The component considered in substep cii) may include the real part, or the imaginary part, or the modulus, or the phase of each complex image forming the stack of images.

Substep civ) may include:

forming an image, called the first maxima image, each pixel of which is associated with a three-dimensional position determined in substep ciii) and is assigned the maximum value determined, in substep ciii), for said three-dimensional position;

selecting, in the first maxima image, pixels the value of which is maximum in a neighbouring zone defined around each pixel; and calculating, for each selected pixel, a signal-to-noise ratio depending on said maximum value and the value of pixels of the first maxima image located in a calculation zone lying around said pixel;

such that each three-dimensional position is selected depending on the signal-to-noise ratio calculated for the pixel of the first maxima image that is associated therewith. The step of selecting pixels is optional, but preferable, and the signal-to-noise ratio may be calculated for all the pixels of the maxima image. A position the associated pixel of which, in the first maxima image, is not selected, is invalidated.

According to one embodiment, step d) may include acquiring, with the image sensor, a second image, each pixel of which is associated with a radial coordinate in the detection plane. According to this embodiment, step d) includes the following substeps:

di) obtaining a second image of interest from the acquired second image and applying a digital propagation operator to the second image of interest in order to propagate it, by a plurality of reconstruction distances, along the propagation axis, so as to obtain a second stack of reconstructed complex images, called the second stack of images, including as many reconstructed complex images as there are reconstruction distances, each reconstructed complex image being representative of an exposure light wave to which the image sensor is exposed at the second time;

dii) for at least one radial coordinate defined by the second image of interest, determining a reconstruction distance that maximizes the variation in a component of each complex image forming the second stack of images, along an axis parallel to the propagation axis and passing through said radial coordinate, said reconstruction distance forming a transverse coordinate associated with said radial coordinate, the value of the component calculated at said reconstruction distance being what is called a maximum value associated with said radial coordinate, substep dii) being carried out for all or some radial coordinates associated with the pixels of the second image of interest;

diii) establishing a list of three-dimensional positions, each three-dimensional position including a radial coordinate and the associated transverse coordinate determined in substep dii), each three-dimensional position being associated with the maximum value obtained in substep dii); and div) selecting three-dimensional positions depending on the maximum value that is associated therewith.

In substep di), the second image of interest may be:

the acquired second image;

or the acquired second image, from which is subtracted an image of the fluidic chamber, acquired by the image sensor, prior or subsequently to the acquisition of the second image, the subtraction being weighted by a weighting term;

or the acquired second image, from which is subtracted an average of images acquired prior and subsequently to the acquisition of the second image, respectively.

In substep dii), the component may include the real part, or the imaginary part, or the modulus, or the phase of each complex image forming the stack of images.

Substep div) may include:

forming an image, called the second maxima image, each pixel of which is associated with a three-dimensional position determined in substep diii) and is assigned the maximum value determined, in substep diii), for said three-dimensional position;

selecting, in the second maxima image, pixels the value of which is maximum in a neighbouring zone defined around each pixel; and calculating, for each selected pixel, a signal-to-noise ratio depending on said maximum value and the value of pixels of the second maxima image located in a calculation zone lying around said pixel;

such that each three-dimensional position is selected depending on the signal-to-noise ratio calculated for the pixel of the second maxima image that is associated therewith. The selecting step is optional, but preferable, and the signal-to-noise ratio may be calculated for all the pixels of the maxima image. A position the associated pixel of which, in the second maxima image, is not selected, is invalidated.

According to one embodiment:
step b) includes two successive illuminations of the fluidic chamber with the light source, at the first time and at the second time, such that the first image represents the exposure wave at each of these times; and
steps c) and d) are merged into one and the same step of obtaining coordinates of particles at the first time and at the second time.

The method may include one of the following features alone or in any technically possible combination:
step e) may include a comparison of the coordinates of particles in the fluidic chamber determined at the first time and at the second time, so as to establish a list of potential movements of the particles between said times;
step g) includes determining a movement range using the movement model taken into account in step f), the potential movements being validated when they are comprised in said movement range;
step g) includes subtracting, from each potential movement, a movement according to the movement model.

According to one embodiment, the fluid includes particles, each particle having a property and moving, with respect to the fluid, according to a movement model, called the particulate movement model, dependent on said property. According to this embodiment, the method includes, on the basis of movements validated in step g), a step i) of taking into account at least one particulate movement model, so as to count the particles depending on a value of said property. According to one variant, the method includes, on the basis of potential movements determined in step e), a step e') of taking into account at least one particulate movement model, so as to count the particles depending on a value of said property. The property is a mass or an electric charge, or an aptitude to move in the fluid.

According to this embodiment, the method may include:
  taking into account a particulate movement model for a preset value of the property; and
  calculating discrepancies in the movements of each particle with respect to the particulate movement model;
such that the property of each particle is determined depending on said discrepancies and said preset value of the property.

The fluid may flow in a flow direction, and the particulate movement may occur in another direction non-parallel to said flow direction.

The method may be such that no image-forming optics is placed between the image sensor in the fluidic chamber. It may also be such that the image sensor includes an image-forming optic between the image sensor and the fluidic chamber, the image formed in step b) being a defocused image.

Another subject of the invention is a device for counting particles flowing through a fluidic chamber, the device including:
  a light source configured to illuminate the fluidic chamber; and
  an image sensor lying in a detection plane, the fluidic chamber being interposed between the image sensor and the light source, the image sensor being configured to acquire a plurality of images of the fluidic chamber illuminated by the light source, at one time or at successive times,
  the device including a processor able to implement steps c) to e) or c) to h) of a method such as described in this patent application, on the basis of at least one image acquired by the image sensor.

Another subject of the invention is a device for observing particles flowing through a fluidic chamber including the following steps:
  placing the fluidic chamber between a light source and an image sensor, the image sensor lying in a detection plane;
  illuminating the fluidic chamber with the light source, the light source emitting an incident light wave that propagates along a propagation axis and acquiring, with the image sensor, an image representative of a light wave, called the exposure wave, to which the image sensor is exposed, the image sensor including various pixels, each pixel being associated with a radial coordinate in the detection plane;
  selecting an image, acquired at an acquisition time, and forming an image of interest by subtracting, from the selected image, an image acquired at a time subsequent to and/or an image acquired at a time prior to the acquisition time, the subtraction possibly being weighted by a weighting term that is for example comprised between 0 and 1;
  applying a digital propagation operator to the image of interest in order to propagate it by a plurality of reconstruction distances, so as to obtain a stack of reconstructed complex images, called the stack of images, including as many reconstructed complex images as there are reconstruction distances, each reconstructed complex image being representative of an exposure light wave to which the image sensor is exposed;
  for at least one radial coordinate defined by the image of interest, determining a reconstruction distance that maximizes the variation in a component of each complex image forming the stack of images, along an axis parallel to the propagation axis and passing through said radial coordinate, the component including the real part of each complex image, or its opposite, said determined reconstruction distance forming a transverse coordinate associated with said radial coordinate, the value of the component calculated at said reconstruction distance being what is called a maximum value associated with said radial coordinate, this step being carried out for all or some of the radial coordinates associated with the pixels of the image of interest;
  establishing a list of three-dimensional positions, each three-dimensional position including a radial coordinate and the associated transverse coordinate determined in the preceding step, each three-dimensional position being associated with the maximum value obtained in the preceding step; and
  selecting three-dimensional positions depending on the maximum value that is associated therewith.

Three-dimensional positions may be selected by forming a maxima image and by determining a signal-to-noise ratio for each pixel of the maxima image, as described above.

Other advantages and features will become more clearly apparent from the following description of particular embodiments of the invention, which are given by way of nonlimiting example, and shown in the figures listed below.

FIGURES

FIG. 1A shows an example of a device allowing the invention to be implemented. FIG. 1B is a detail of FIG. 1A.

FIG. 2A illustrates a succession of steps allowing a first embodiment of the method to be implemented. FIGS. 2B, 2C and 2D show profiles of a portion of an acquired image lying about a hologram corresponding to a particle, at three successive times. FIG. 2E shows a profile corresponding to a stationary component, obtained by combining the profiles of FIGS. 2B to 2D. FIG. 2F shows a profile corresponding to a mobile component, this profile being obtained by subtracting the stationary component, as shown in FIG. 2D, from the profile of FIG. 2C. FIG. 2G shows a profile modelling the variation in the modulus of a complex image reconstructed from an image corresponding to the profile shown in FIG. 2F. FIG. 2H shows a profile modelling the variation in the opposite of the real part of a complex image reconstructed from an image corresponding to the profile shown in FIG. 2F.

FIG. 3A shows a fluidic chamber employed in a first experimental trial. FIG. 3B is a plot of results obtained in the first experimental trial. FIG. 3C shows the impact of a value of a threshold on the performance of the count.

SUMMARY OF PARTICULAR EMBODIMENTS

Figure 1A:
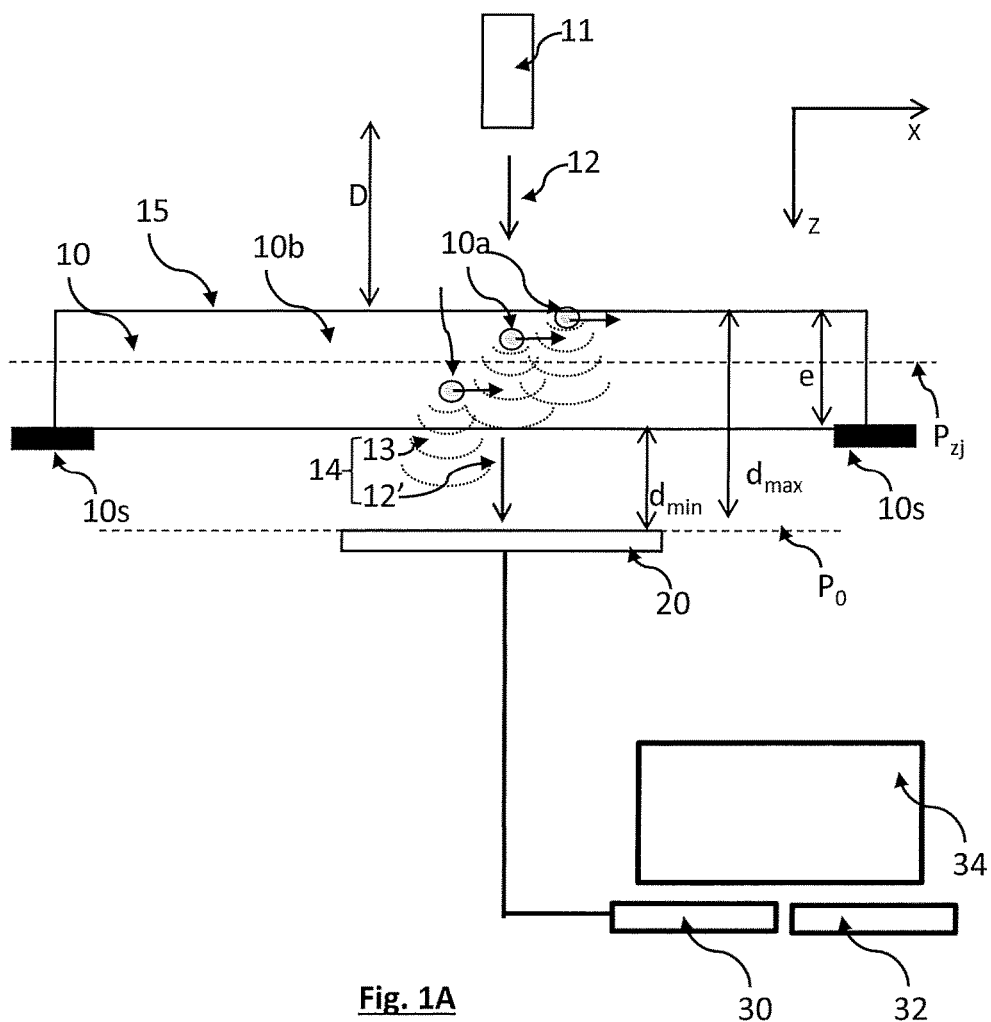

FIG. 1A shows an example of a device allowing an implementation of the invention. A light source 11 is able to emit a light wave 12, called the incident light wave, that propagates towards a sample 10, along a propagation axis Z. The light wave is emitted in a spectral band $\Delta\lambda$.

The sample 10 is a sample including particles 10a that it is desired to count, the particles being placed in a transparent or translucent carrier fluidic medium 10b. The particles are elements of small size, and are inscribed in a diameter comprised between 0.1 µm and 100 µm; or between 1 µm and 100 µm. The particles are solids or liquids. It may be a question of dusts, or of cells or of microorganisms or of microbeads, usually employed in biological applications, or even of microalgae. It may also be a question of droplets insoluble in the fluid 10b, for example droplets of oil dispersed in an aqueous phase. The carrier medium 10b is a fluid, for example air or a liquid, for example water or a biological liquid. The sample may for example be an aerosol, including particles in suspension in a gas, the latter possibly in particular being air.

The sample 10 is contained in a fluidic chamber 15. The thickness e of the sample 10, along the propagation axis, typically varies between 10 µm and 2 cm or 3 cm, and is preferably comprised between 20 µm and 1 cm. The sample lies in a plane, called the plane of the sample, that is preferably perpendicular to the propagation axis Z. The fluidic chamber 15 is held on a holder 10s facing the image sensor 20.

Since they are carried by the fluid 10b, the latter being mobile in the fluidic chamber 15, the particles 10a are mobile in the fluidic chamber 15. In this example, the fluid flows, in the fluidic chamber 15, along a longitudinal flow axis X. The particles 10a are thus entrained by the fluidic movement of the medium 10b, the latter acting as carrier medium, and forming a fluidic current in the interior of the fluidic chamber 15. The movement of the medium is modelable. The particles 10a may also be mobile with respect to the medium 10b, the movement of the particles with respect to the fluid that carries them being designated by the term particulate movement. Thus, the movement of the particles 10a in the fluidic chamber 15 is not random and obeys a preset movement model, combining the fluidic movement of the medium 10b and, possibly, the particulate movement of the particles with respect to the fluid.

The distance D between the light source 11 and the sample 10 is preferably larger than 1 cm. It is preferably comprised between 2 and 30 cm. Advantageously, the light source, seen by the sample, may be considered to be point-like. This means that its diameter (or its diagonal) is preferably smaller than one tenth, better still one hundredth, of the distance between the sample and the light source. In the shown example, the light source 11 is a laser diode. According to one variant, the light source 11 is a white light source or a light-emitting diode. In this case, a spatial filter is advantageously placed between the light source and the sample, so that the light source appears to be point-like. The spatial filter may be a pinhole or an optical fiber. A wavelength filter is also preferably placed between the light source and the sample, in order to adjust the spectral emission band $\Delta\lambda$ of the incident light wave 12. Preferably, the spectral emission band $\Delta\lambda$ of the incident light wave 12 has a width smaller than 100 nm. By spectral bandwidth, what is meant is a full width at half maximum of said spectral band.

The fluidic chamber 15 is placed between the light source 11 and the aforementioned image sensor 20. The latter is preferably parallel, or substantially parallel, to the plane in which the sample lies. The term substantially parallel means that the two elements may not be rigorously parallel, an angular tolerance of a few degrees, smaller than 20° or 10°, being acceptable. The image sensor 20 is able to form an image I in a detection plane $P_0$. As shown in FIG. 18B, the image sensor includes a matrix-array of pixels, each pixel being associated with coordinates (x, y), called radial coordinates, in the detection plane $P_0$. The image sensor may in particular be a CCD or CMOS sensor. The detection plane $P_0$ is preferably perpendicular to the propagation axis Z of the incident light wave 12. The distance between the sample 10 and the pixel matrix-array of the image sensor 20 is comprised between a minimum distance $d_{min}$ and a maximum distance $d_{max}$. The thickness e of the fluidic chamber corresponds to the difference between $d_{max}$ and $d_{min}$. $d_{min}$ may be comprised between 50 µm and 2 cm and is preferably comprised between 100 µm and 2 mm. The thickness of the fluidic chamber is generally comprised between 100 µm and 5 cm.

The absence of image-forming optical system and in particular of magnifying optics between the image sensor 20 and the sample 10 will be noted. This does not prevent focusing microlenses optionally being present level with each pixel of the image sensor 20, said microlenses not having the function of magnifying the image acquired by the image sensor. The image sensor 20 is thus placed in what is called a lensless imaging configuration. Such a configuration allows a large field of observation to be obtained. Other configurations are nevertheless envisionable, in particular a configuration in which a focusing optic is interposed between the image sensor 20 and the fluidic chamber 15. In such a configuration, the image sensor acquires a defocused image of the sample 10.

Under the effect of the incident light wave 12, the particles present in the fluidic chamber 15 may generate a diffracted wave 13 that is liable, level with the detection plane $P_0$, to interfere with a portion of the incident light wave 12 transmitted by the sample. Moreover, the sample may absorb some of the incident light wave 12. Thus, the light wave 14, called the exposure light wave, transmitted by the sample 10 and to which the image sensor 20 is exposed, may comprise:
- a component 13 resulting from the diffraction of the incident light wave 12 by each particle of the sample; and
- a component 12' resulting from the absorption of the incident light wave 12 by the sample.

These components interfere in the detection plane. Thus, the image I acquired by the image sensor 20 includes interference patterns (or diffraction patterns), each interference pattern being generated by one particle 10a of the sample 10.

A processor 30, for example a microprocessor, is configured to process each image I acquired by the image sensor 20. In particular, the processor is a microprocessor connected to a programmable memory 32 in which is stored a sequence of instructions for carrying out the image processing operations and calculations described in this description. The processor may be coupled to a screen 34 allowing images acquired by the image sensor 20 or calculated by the processor 30 to be displayed.

The fluidic chamber 15 is stationary with respect to the image sensor 20. Thus, the fluidic medium 10b and the particles 10a flowing through the fluidic chamber are in motion with respect to the image sensor 20.

As indicated with reference to the prior art, it is possible to apply, to each image acquired by the image sensor, a propagation operator h, so as to calculate a complex quantity representative of the exposure light wave 14. It is then possible to calculate a complex expression A for the light wave 14 at every point of spatial coordinates (x, y, z) and in particular on a reconstruction surface lying facing the image sensor 20. The reconstruction surface is usually a plane $P_z$, called the reconstruction plane lying parallel to the image sensor 20 at a coordinate z from the detection plane $P_0$. The reconstruction plane $P_z$ is then parallel to the detection plane $P_0$. An image called the complex image $A_z$, which is representative of the exposure light wave 14 in the reconstruction plane $P_z$, is then obtained. The complex image $A_z$ is obtained by convoluting the image I acquired by the image sensor 20 with the propagation operator h, according to the expression: $A_z = I*h$.

The propagation operator h describes the propagation of the light between the detection plane $P_0$ and the reconstruction plane $P_z$. In this example, the equation of the detection plane $P_0$ is z=0.

The propagation operator is for example what is called a Fresnel operator, defined by the following expression $$h_z(x, y) = \frac{-i}{\lambda z} e^{\frac{i\pi}{\lambda z}(x^2+y^2)}. \quad (1)$$

One particularity of the invention is that, since they are entrained by the fluid 10b, the particles 10a move. The fluid moves between an inlet and an outlet of the fluidic chamber 15, along a flow axis X. In order to count them, it is necessary to obtain three-dimensional positions of the particles at a first time $t_1$ and at a second time $t_2$ subsequent to the first time, the time delay $\Delta t = t_2 - t_1$ between the two times depending on a maximum speed $V_{max}$ of the fluid in the fluidic chamber 15 and on the size of the portion of the fluidic chamber seen by the sensor. If L is a dimension of the fluidic chamber 15, seen by the image sensor 20, along the propagation axis X of the fluid, it is preferable that:

$$\Delta t < \frac{L}{2} V_{max}.$$

Various embodiments are envisionable. According to a first embodiment, the image sensor acquires two successive images $I(t_1)$ and $I(t_2)$ at the first time $t_1$ and at the second time $t_2$, respectively. From each image, three-dimensional coordinates of particles at each time are obtained. According to a second embodiment, one and the same image of the fluidic chamber is acquired at two times, this image being acquired at the first time and the second time.

Figure 2A:
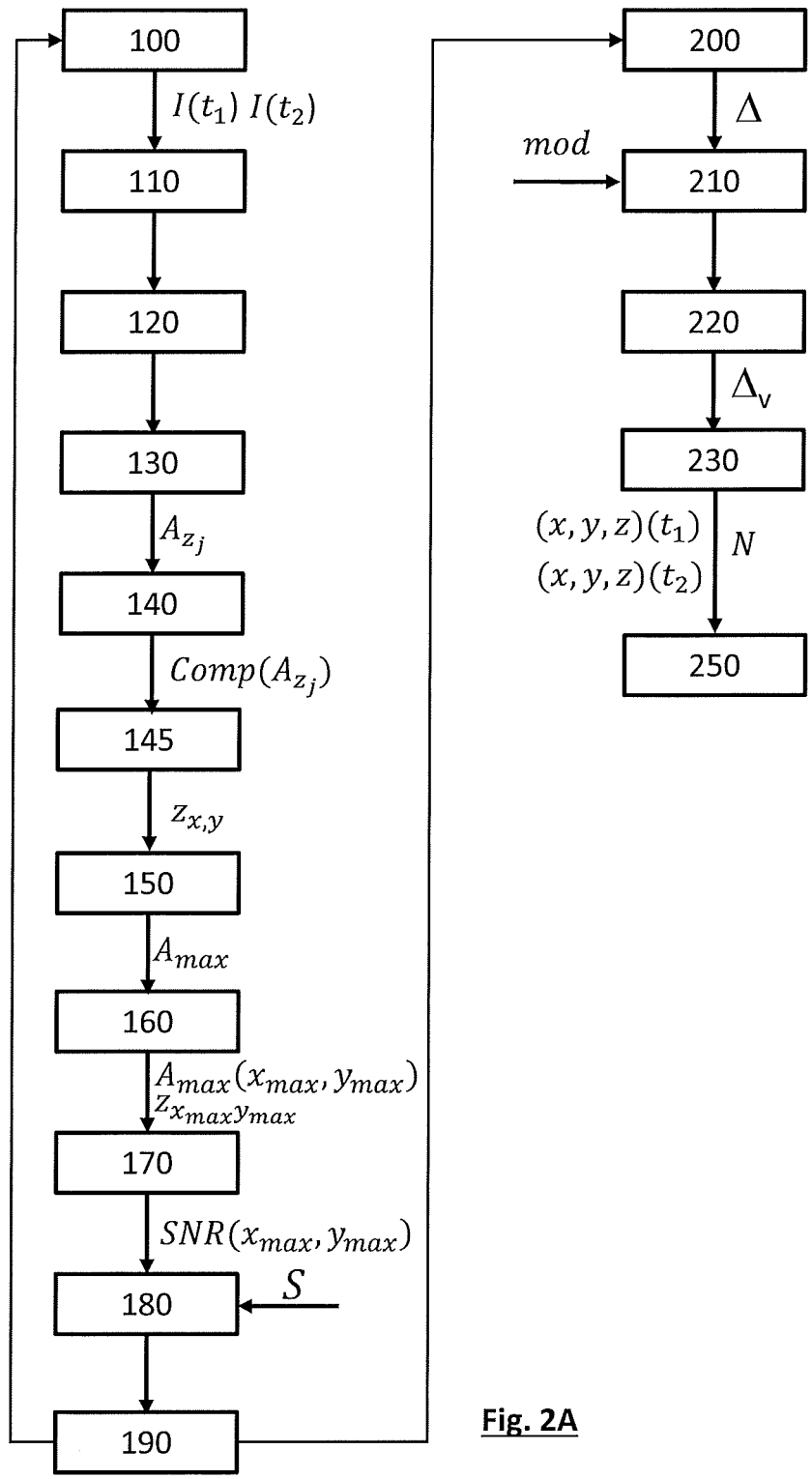

The main steps of the first embodiment of the method are described below, with reference to FIG. 2A.

Step 100: acquisition. It is a question of acquiring an image $I(t_i)$ at various times $t_i$ at an acquisition frequency. In a first iteration, the time $t_i$ is a first time $t_1$ and an image called the first image $I(t_1)$ is acquired. In a second iteration, the time $t_i$ is a second time $t_2$, the second time being subsequent to the first time. The image acquired at the time $t_2$ is a second image $I(t_2)$.

Step 110: an image of interest is extracted from the acquired image, the image of interest representing a mobile component $I_m(t_i)$ of the acquired image. The acquired image $I(t_i)$ includes a component $I_f(t_i)$, called the stationary component, representing elements considered to be independent of time, and a component $I_m(t_i)$, called the mobile component, representing elements considered to be in motion in the image. The particles moving in the sample are in motion and form the motion component. The first filtering operation aims to remove the stationary component from the acquired image. The stationary component may be obtained by means of one or more images acquired at various times different from the acquisition time of the filtered image. The stationary component $I_f(t_i)$ may be estimated via an initial image $I(t_0)$ acquired while no particles are flowing through the fluidic chamber 15. This allows an image of stationary elements, for example dust, not representative of the mobile particles to be counted to be obtained. Preferably, the stationary component $I_f(t_i)$ is estimated via an average of an image acquired at a time prior to and an image acquired at a time subsequent to the acquisition time $t_i$ of the acquired image. It may for example be a question of the time $t_{i-1}$ preceding and the time $t_{i+1}$ following the acquisition time $t_i$, in which case the stationary component is such that $$I_f(t_i) = \frac{I(t_{i+1}) + I(t_{i-1})}{2}. \quad (2)$$

The estimation of the stationary component is thus renewed with each new acquisition of an image. It corresponds to an average of two images acquired before and after the acquired image in question, respectively, the average being weighted by a weighting factor of ½. This allows the stationary component to be regularly updated.

The stationary component is subtracted from each acquired image, so as to obtain a mobile component $I_v$ that is representative of the mobile elements in the image, and in particular of the mobile particles. $I_v(t_i) = I(t_i) - I_f(t_i)$ (3).

The mobile component forms an image of interest on the basis of which the following steps are carried out. At the first time $t_1$, the image of interest is denoted $I_v(t_1)$. At the second time $t_2$, the image of interest is denoted $I_v(t_2)$.

Figure 2B:
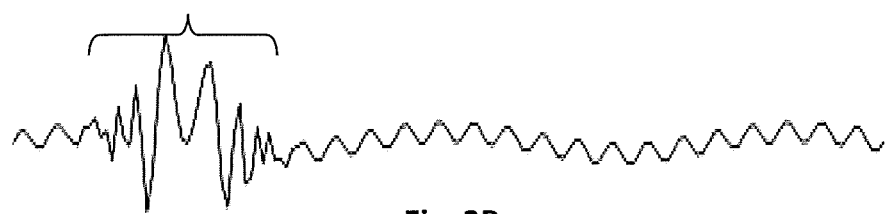
Figure 2C:
Figure 2D:
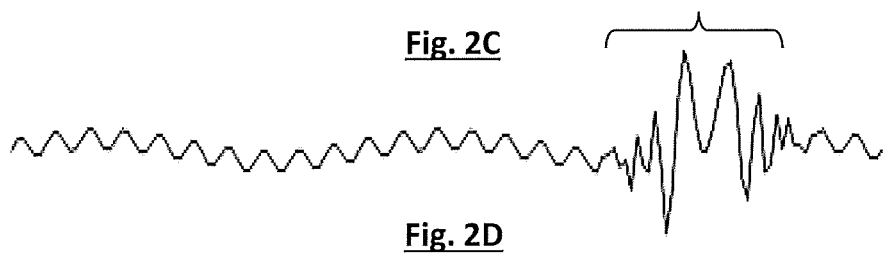
Figure 2E:
Figure 2F:
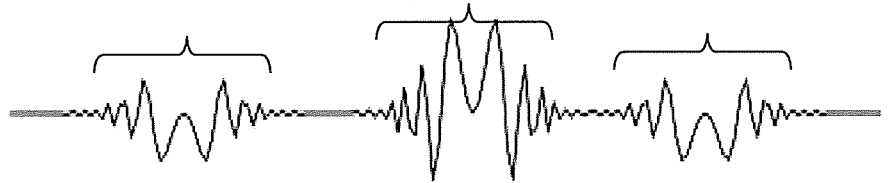

FIGS. 2B to 2D show modelled examples of intensity profiles of a hologram, corresponding to one particle, in an image acquired by the image sensor 20, at the times $t_{i-1}$, $t_i$, and $t_{i+1}$, respectively. The particle is moving along the flow axis X of the fluid, this resulting in a translation of the hologram, the latter being represented by a curly bracket in each of these figures. The undulations observed on either side of the hologram correspond to the effect of imperfections in the apparatus used. These imperfections are in particular lighting nonuniformities and the interference between reflections taking place at the interfaces of the chamber. This is reflected by the fact that in FIGS. 2B, 2C and 2D, the profiles are, level with the holograms, asymmetric and different. FIG. 2E shows the stationary component $I_f(t_i)$ such as determined according to expression (2). The stationary component $I_f(t_i)$ includes the effect of the imperfections of the apparatus and the holograms corresponding to the times $t_{i-1}$ and $t_{i+1}$, the latter being weighted by a weighting factor equal to ½. FIG. 2F shows the mobile component $I_v(t_i)$ obtained according to expression (3). It may be seen that the effect of the imperfections has disappeared. The central hologram, corresponding to the position of the particle at the time $t_i$, is symmetric. The holograms corresponding to the times $t_{i-1}$ and $t_{i+1}$ are also symmetric and are weighted with a weighting factor equal to −½. These residual holograms are called echoes.

Thus, this step allows a mobile component $I_v(t_i)$ of the acquired image to be estimated, this mobile component being representative of elements that are mobile, with respect to the image sensor, at the acquisition time $t_i$. This mobile component $I_v(t_i)$ allows the mobile particles that it is sought to count to be better seen.

Step 120: frequency filtering. The image of interest $I_v(t_i)$ resulting from step 110 is subjected to a passband frequency filtering operation: such a filtering operation allows low spatial frequencies, associated with nonuniformities in the illumination of the sample, and high spatial frequencies, the latter being considered to be noise, to be removed. The passband of the frequency filter is preferably comprised between a low cut-off frequency and a high cut-off frequency. The low cut-off frequency may be equal to 0.02 f. The high cut-off frequency may be equal to 0.5 f. f is a frequency corresponding to half the spatial frequency defined by the size of the pixels:

$$f = \frac{1}{2l}, l$$

being a dimension (length or width) of a pixel.

Step 130: propagation of the filtered image. The image resulting from step 120 is propagated by various reconstruction distances $z_j$ along the propagation axis Z. The reconstruction distances are determined such that the reconstruction planes $P_{z_j}$ respectively associated with each reconstruction distance $z_j$ are comprised in the sample. Thus, from each acquired image $I(t_i)$, after the steps of extracting the image of interest 120 and filtering 130, a stack of complex images $A_{z_j}(t_i)$ reconstructed at various reconstruction distances $z_j$ is formed. If $d_{min}$ and $d_{max}$ are respectively the minimum distance and the maximum distance between the sample and the image sensor, the reconstruction is carried out so as to obtain various reconstruction planes between $d_{min}$ and $d_{max}$. As described below, the spatial resolution with which the coordinates of the particles are determined depends on the number of reconstruction distances considered. The interval between two different reconstruction distances may for example be 100 μm. At the end of this step, a stack of complex images is obtained, each complex image lying parallel to the detection plane, at a coordinate $z_j$ called the transverse coordinate.

Step 140: Extraction of a component of each complex image. It is a question of associating, with each pixel of the complex image, a real number. Thus, the stack of complex images $A_{z_j}(t_i)$ is replaced with a stack of images $A'_{z_j}(t_i)$ of real numbers, each pixel $A'_{z_j}(t_i, x, y)$ of each real image being a component comp($A'_{z_j}(t_i, x, y)$) of a complex image $A_{z_j}(t_i)$, at the transverse coordinate $z_j$ and at a given radial coordinate (x, y) (i.e. for a given pixel). By component of a complex image, what is meant is a quantity obtained from the complex image at the radial coordinate (x, y). The component may be or include the real part, the imaginary part, or the modulus, or the phase, of the complex amplitude $A_{z_j}(x, y)$ of the complex image $A_{z_j}(t_i)$ at the radial position (x, y). The component may combine quantities listed in the preceding sentence. It is sought here to obtain a transverse coordinate $z_j$ denoted $z_{xy}$, that maximizes the component, and to do so for each radial coordinate (x, y). This maximization is carried out in step 145.

Figure 2G:
Figure 2H:
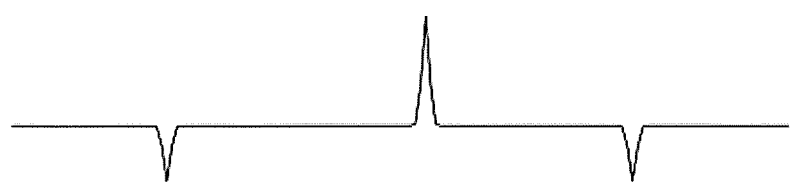

FIGS. 2G and 2H both show a profile of a component of a reconstructed complex image, at a radial coordinate $z_j$, the complex image being obtained by holographic reconstruction of the image $I_v(t_i)$ the profile of which is shown in FIG. 2F. FIG. 2G shows the profile of the modulus of the reconstructed complex image. FIG. 2H shows the profile of the opposite of the real part of the reconstructed complex image. In other words, FIGS. 2G and 2H show the profile of an image of real numbers that are obtained after extraction of a component from the reconstructed complex image, the component being the modulus $|A_{z_j}(x, y)|$ or the opposite of the real part $-\text{Re}(A_{z_j}(x, y))$, respectively. It may be seen that when the component is the opposite of the real part, the central hologram, visible in the profile of FIG. 2H, is represented by a high positive value. The holograms located on either side of the central hologram correspond to residues, or echoes, resulting from the extraction of the image of the mobile component. Their amplitude is lower than that of the central hologram, and is negative. It will be understood that it will be easier to discriminate the central hologram, corresponding to the particle at the time $t_i$, from the holograms corresponding to a residue (or echo) of the particle at the prior time $t_{i-1}$ and subsequent time $t_{i+1}$, these holograms not being representative of the particle at the time $t_i$. In the profile of FIG. 2G, the hologram of the particle at the time $t_i$ results in a peak of high positive amplitude, whereas the holograms of the particle at the prior time $t_{i-1}$ and subsequent time $t_{i+1}$ result in peaks of lower but likewise positive amplitude. It will be understood that it is more difficult to discriminate, on the basis of the modulus, between the "useful" holograms, i.e. corresponding to a position of the particle, and the holograms of echoes, corresponding to a position of a particle at a prior or subsequent time.

Comparison of FIGS. 2G and 2H shows that it is advantageous, in particular with respect to conventional holographic reconstruction techniques, in which the modulus of a complex amplitude is considered, to consider the real part or its opposite. Specifically, in contrast to a modulus, a real part of an image is signed in the sense that it may be positive or negative. It allows discrimination to be carried out on the basis of a sign, this not being possible when moduli are considered. Taking into account the real part would appear to be particularly relevant when subsequent to arithmetic combinations of images including a subtraction of images.

Step 145: Digital focusing. In this step, it is sought, for each pixel of the acquired image, i.e. for each radial position (x, y), to find a transverse coordinate z, along the propagation axis Z, for which the component comp($A_{z_j}(t_i)$) of a complex image $A_{z_j}$ of the stack of images, for the pixel of coordinates (x, y), is maximum. It is a question of applying a technique called digital focusing known to those skilled in the art. A particle is present at an unknown distance from the image sensor. The closer the reconstruction distance gets to this distance, the more the particle forms, in the reconstructed complex image, a narrow and intense spot. Since the complex image includes a real part and an imaginary part, the distance separating the particle from the detector is sought by analyzing the spatial variation in a component of each complex image along the propagation axis.

In other words, $z_{xy}$ is determined such that:

$$z_{xy} = \underset{z_j}{\operatorname{argmax}}(comp(A_{z_j}(x, y))) = \underset{z_j}{\operatorname{argmax}}(-Re(A_{z_j}(x, y))). \quad (4)$$

This step is repeated for all or some of the radial positions (x, y) of the image sensor so that each radial coordinate (x, y) is associated with a transverse coordinate $z_{xy}$ such as defined in expression (4).

Step 150: formation of the maxima image.

Following step 145, an image, called the maxima image, is formed, this image being such that $$A_{max}(x,y) = comp(A_{z_{xy}}(x,y)) = -Re(A_{z_{xy}}(x,y)) \quad (5).$$

This image includes, for each pixel (x, y), the maximum value of the component, in the stack of complex images $A_{z_j}$, along the propagation axis Z, i.e. the value determined in step 145. Each pixel (x, y) of the maxima image $A_{max}$ is associated with the transverse coordinate $z_{xy}$ identified in step 145.

In the first iteration ($t_i = t_1$), a first maxima image is obtained. In the second iteration ($t_i = t_2$) a second maxima image is obtained.

Step 160: search for local maxima in the maxima image.

In this step, groups of adjacent pixels are searched for local maximum values. For example, each group of pixels includes 51×51 adjacent pixels. A pixel of the maxima image $A_{max}$ is considered to be a local maximum if it is the pixel with the highest value in a group of 51×51 pixels centered on said pixel. The maxima image $A_{max}$ may be subjected to a smoothing operation before the local maxima are sought. It may be a question of smoothing achieved by applying a Gaussian filter or a lowpass filter.

It is thus possible to obtain: a list of the coordinates of each local maximum pixel ($x_{max}$, $y_{max}$) and the value $A_{max}(x_{max}, y_{max})$ of the maxima image $A_{max}$ for this pixel; and the transverse coordinate $z_{x_{max}y_{max}}$ associated with this pixel. Other known digital focusing algorithms allowing such a list to be defined may be applied to the stack of images resulting from step 140. Such algorithms may for example be based on a criterion of clearness of each image of the stack of images. These algorithms also allow local maxima and a transverse coordinate associated with these local maxima to be defined.

Step 170: taking into account the signal-to-noise ratio.

The search for local maxima in the maxima image $A_{max}$ will possibly be carried out on a nonuniform background. This nonuniform background is in particular caused by fluctuations in interference fringes produced by the multiple interfaces between the light source 11 and the image sensor 20. Thus, the inventors have deemed that it would be preferable to take into account a signal-to-noise ratio at each radial coordinate determined in step 160. Thus, at each radial position $x_{max}$, $y_{max}$ defined in step 160, a signal-to-noise ratio SNR($x_{max}$, $y_{max}$) is calculated, this ratio being calculated using information contained in the maxima image $A_{max}$. A local noise level is calculated, in the maxima image, around each radial position ($x_{max}$, $y_{max}$), for example in a noise-calculation zone centered on the position ($x_{max}$, $y_{max}$) and of diameter equal to 200 pixels. The pixels considered for the calculation of local noise may be all of the pixels in the noise-calculation zone, or certain pixels in this zone. The inventors have for example taken into account 100 pixels regularly distributed around the circle bounding the noise-calculation zone, the noise level being estimated via a calculation of the median of the value of these 100 pixels.

This step allows a list of radial coordinates ($x_{max}$, $y_{max}$) corresponding to a local maximum in the maxima image to be established, each pair of radial coordinates being associated with a transverse coordinate $z_{x_{max}y_{max}}$. A list of three-dimensional positions ($x_{max}$, $y_{max}$, $z_{x_{max}y_{max}}$) in the sample liable to include a particle is then obtained. With each three-dimensional position ($x_{max}$, $y_{max}$, $z_{x_{max}y_{max}}$) is associated an estimation of the signal-to-noise ratio SNR($x_{max}$, $y_{max}$) of the image $A_{max}$ and the position ($x_{max}$, $y_{max}$). Each of these three-dimensional positions is liable to be occupied by a particle 10a at the time $t_i$ in question.

Step 180: thresholding. In this step, the signal-to-noise ratios that are respectively assigned to the three-dimensional positions are thresholded. The thresholding is carried out depending on a threshold value S that may be preset. Only those three-dimensional positions the associated signal-to-noise ratio of which is higher than the threshold value are retained, the others being considered not to be representative of particles. The threshold may be preset, for example on the basis of calibrations, or optimized as described below with regard to step 250.

Step 190: reiteration. Steps 110 to 180 are reiterated on the basis of an image $I(t_2)$ acquired at the second time $t_2$. This allows a list of three-dimensional positions ($x_{max}$, $y_{max}$, $z_{x_{max}y_{max}}$) at the time $t_2$, and a signal-to-noise ratio associated with each position, to be obtained. Thus, at the end of step 190 the following will have been obtained: a first list of three-dimensional positions ($x_{max}$, $y_{max}$, $z_{x_{max}y_{max}}$)($t_1$) at the first time $t_1$; a second list of three-dimensional positions ($x_{max}$, $y_{max}$, $z_{x_{max}y_{max}}$)($t_2$) at the second time $t_2$; and a signal-to-noise ratio associated with each position.

Step 200: Calculation of potential movements. In this step, potential movements $\Delta$ are determined by comparing each three-dimensional position at the first time ($x_{max}$, $y_{max}$, $z_{x_{max}y_{max}}$)($t_1$) to each three-dimensional position at the second time ($x_{max}$, $y_{max}$, $z_{x_{max}y_{max}}$)($t_2$). This results in a list of vectors of potential movements, the coordinates of which represent potential movements. FIG. 3B shows vectors of movements the coordinates of which are indicated along the axis X (abscissa axis) and the axis Z (ordinate axis). Each movement vector corresponds to a pair comprising a three-dimensional position of a particle ($x_{max}$, $y_{max}$, $z_{x_{max}y_{max}}$)($t_1$) at the first time, chosen from the first list, and an another three-dimensional position of a particle ($x_{max}$, $y_{max}$, $z_{x_{max}y_{max}}$)($t_2$) at the second time, chosen from the second list. A first screening is carried out, on the basis of a minimum movement and a maximum movement along each axis, and on the basis of a criterion relating to the signal-to-noise ratio assigned to each three-dimensional position: the signal-to-noise ratio SNR($x_{max}$, $y_{max}$) of the position at the first time must correspond, to within an uncertainty, to the signal-to-noise ratio assigned to the position at the second time.

Step 210: Taking into account a movement model mod. It is a question of employing knowledge of kinematic parameters of the movement of the particles 10a in the fluidic chamber 15. For example, the medium 10b in which the particles 10a are located is moving through the fluidic chamber 15, the medium 10b carrying the particles. The movement of the medium 10b may be modelled, the particles being considered to follow the movement of the medium, at least in a plane. For example, when the fluidic chamber 15 is horizontal, the particles are assumed to follow the model of the movement in the horizontal plane, to within a fluctuation corresponding to a movement of the particles in a vertical plane, the latter being due to gravity and depending on the mass of the particles.

Taking into account the movement model mod allows a movement range, lying between a first limit and a second limit, to be defined. The movement range defines the coordinates of possible movement vectors given the adopted movement model. Potential movements located outside of the movement range are invalidated.

The movement model may be a parametric model, the parameters of which are adjusted experimentally on the basis of a statistical treatment of the movements detected in a series of image acquisitions. FIG. 3B for example shows, in the form of a point cloud, all of the movements obtained following an analysis of a series of 500 image acquisitions. Each movement is represented by a circle the abscissa of which is the component $\Delta x$ of the movement along the longitudinal axis X and the ordinate of which is the coordinate of the reconstruction plane $z_j$ corresponding to the position of the particle at the start of the movement. Points having the same ordinate correspond to movements the starting position of which is located in a plane parallel to the image sensor, located at the distance $z_j$ from the latter. Taking into account multiple image acquisitions allows data relating to the movement to be gathered, the data being statistically significant enough to determine or adjust the parameters of the model. The point cloud clearly has a zone of high density that has a boomerang shape.

At the center of the fluidic chamber 15 ($z_j$ close to 35), the movements have a maximum amplitude. At the edges of the fluidic chamber 15 ($z_j$ close to 0 or $z_j$ close to 60), the movements are lesser, because of the presence of the walls of the fluidic chamber. Thus, preferably, the movement model is three-dimensional, so as to take into account a flow-speed distribution of the fluid in a transverse plane YZ perpendicular to the flow axis X of the fluid, in particular because of edge effects resulting from the walls of the fluidic chamber 15.

In this example, the boomerang shape is modelled by a 3rd degree polynomial. The coefficients of this polynomial may be determined via a quadratic adjustment with respect to the measured data. It is thus possible to determine or refine the parameters of the model, on the basis of the acquired images. Thus, a parametric movement model is used, the parameters of the model being determinable or updatable with experimental measurements.

In FIG. 3B a range corresponding to an acceptable tolerance with respect to the model, which is the zone comprised between the curves M1 and M2, has also been shown.

Step 220: movement validation.

In step 220, the potential movements $\Delta$ determined in step 200 are compared to the movement range defined in step 210. Movements not comprised in the movement range are considered to be invalid and are removed. The movements $\Delta_v$ comprised in the range are validated. In the example in FIG. 3B, the movement range is defined in a plane ($\Delta x$, $z_j$), in which case the validation is carried out on the basis of a projection of each potential movement vector onto this plane.

Step 230: definition of the positions and/or the number of particles corresponding to valid movements.

Each movement $\Delta_v$ validated in step 220 allows a position of a particle at the first time and a position of a particle at the second time to be defined. A list of validated positions of particles at the first time (x, y, z)($t_1$) and a list of validated positions of particles at the second time (x, y, z)($t_2$) are then determined. This list is produced by considering that, at the first time and at the second time, a particle is associated with only a single movement. Each list thus obtained allows a position of the particles at the first time, and a position of the particles that the second time, and the number N of particles 10a flowing through the fluidic chamber 15, to be estimated.

Preferably, to validate the position of a particle at a time $t_i$, 3 different times are considered, for example three successive times $t_{i-1}$, $t_i$ and $t_{i+1}$. The time $t_i$ is what is called a current time, the times $t_{i-1}$ and $t_{i+1}$ being times prior to and subsequent to the current time, respectively. On the basis of the movements $\Delta_v(t_{i-1}, t_i)$ validated between $t_{i-1}$ and $t_i$, a first list of pairs of positions between the times $t_{i-1}$ and $t_i$ is established. On the basis of the movements $\Delta_v(t_i, t_{i+1})$ validated between $t_i$ and $t_{i+1}$, a second list of pairs of positions between the times $t_i$ and $t_{i+1}$ is established. The list of particles at the current time $t_i$ is obtained by merging the first list and the second list, duplications being removed.

Step 250: optimization of the threshold

A parameter that may be important for the implementation of the method is the threshold S used in step 180 to select or exclude particle positions. The number of particles considered when establishing potential movements depends on this threshold. FIG. 3C shows a variation in the number of particles that are counted, i.e. the signal-to-noise ratio of which is higher than the value of the abscissa, implementing the method described above. Such a representation allows a posteriori modification of the threshold, the value of the threshold for example being set to an optimal value corresponding to the flattest portion of the curve. The inventors consider that an optimal threshold corresponds to the flattest portion of the curve, i.e. to a low derivative, the derivative being calculated with respect to the value of the threshold. In the example shown in FIG. 3C, and described below, the optimum value of the threshold, implementing the method, is 2.2 or 2.3. It is therefore possible to remove a posteriori particles having a signal-to-noise ratio lower than the threshold.

By way of comparison, the figure also shows a variation in the number of particles N' counted without considering a movement, i.e. on the basis of one image acquired at one given time. It may be seen that taking into account movements allows the number of particles counted to be decreased, in particular when the threshold is low.

Figure 1B:
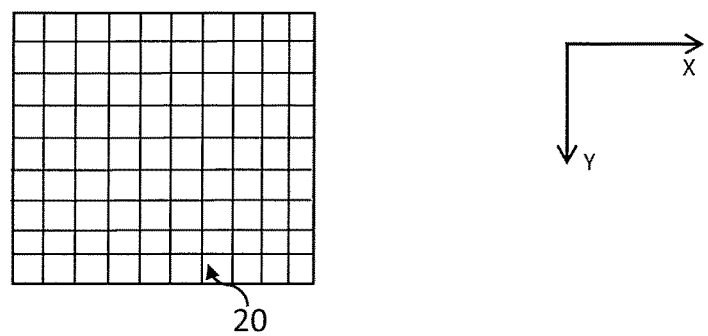
Figure 3A:
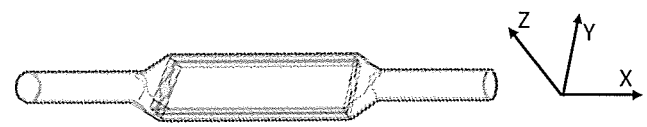
Figure 3B:
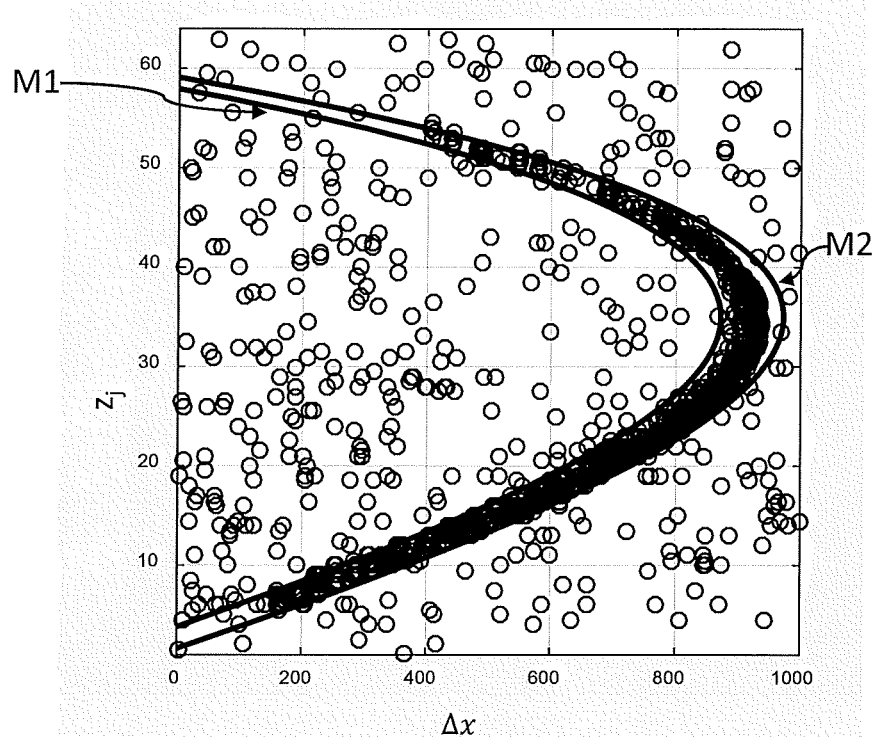
Figure 3C:
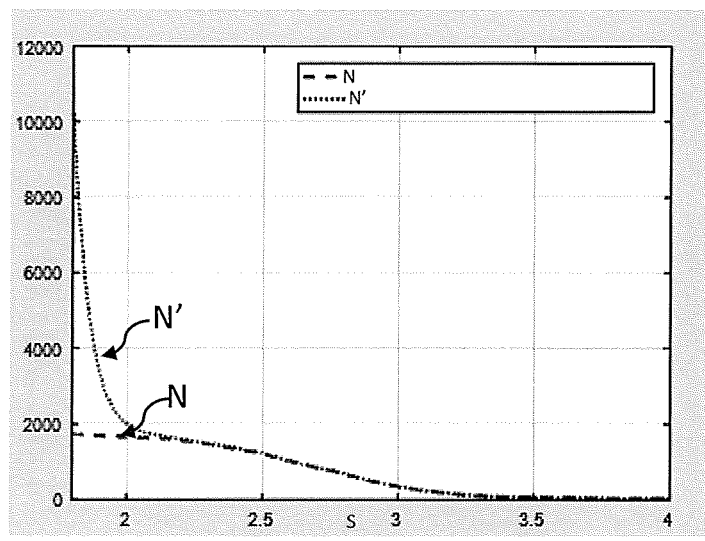

In a first experimental trial a fluidic chamber such as shown in FIG. 3A was used, oriented vertically. The trial was carried out in a configuration such as described in FIG. 1, the axis X, along which the particles propagate, being vertical and oriented downwards.

The sample was made up of polystyrene particles of 1 µm diameter transported in an airflow. The experimental parameters were the following:

Fluidic chamber: Starna type 45-F: inside dimensions of 5×10×45 mm.

Light source: CiviLaser laser diode—405 nm—duration of a pulse 100 µs.
Image sensor: CMOS MIGHTEX BTN-B050-U—2592×1944 pixels of 2.2 µm by 2.2 µm size.
Acquisition frequency: 10 Hz.

64 reconstruction planes, corresponding to distances, with respect to the image sensor, regularly spaced between 1.5 mm and 7.8 mm were used.

At each time a list of particles, of coordinates (x, y, z), was determined. Since the signals were weak, the detection privileged detection of a high proportion of the particles with the drawback of a high number of false detections.

On the basis of the positions of the particles at two successive times, the potential movements Δ were determined, the latter being represented in the form of circles, having a coordinate Δx along the axis X, a coordinate Δz along the axis Z and a coordinate Δy along the axis Y. The potential movements were obtained by taking into account the following screening criteria: 0≤Δx≤2.2 mm; 0≤Δy≤66 µm; 0≤Δz≤200 µm.

FIG. 3B illustrates these potential movements in the form of a point cloud in the plane (Δx, Z). A movement model was taken into account, forming limits represented by the curves M1 and M2 drawn in FIG. 3B. The movements located between these curves were validated.

On the basis of the validated movements Δv the number N of particles was counted as a function of the signal-to-noise-ratio threshold considered in step 180, the variation in the number N of particles counted as a function of the signal-to-noise-ratio threshold S being shown in FIG. 3C. This figure also shows, as a function of the signal-to-noise-ratio threshold, a number of particles N' with the movement not taken into account. It may be seen that beyond a certain threshold the estimation is poor if the movement is not taken into account.

Figure 4A:
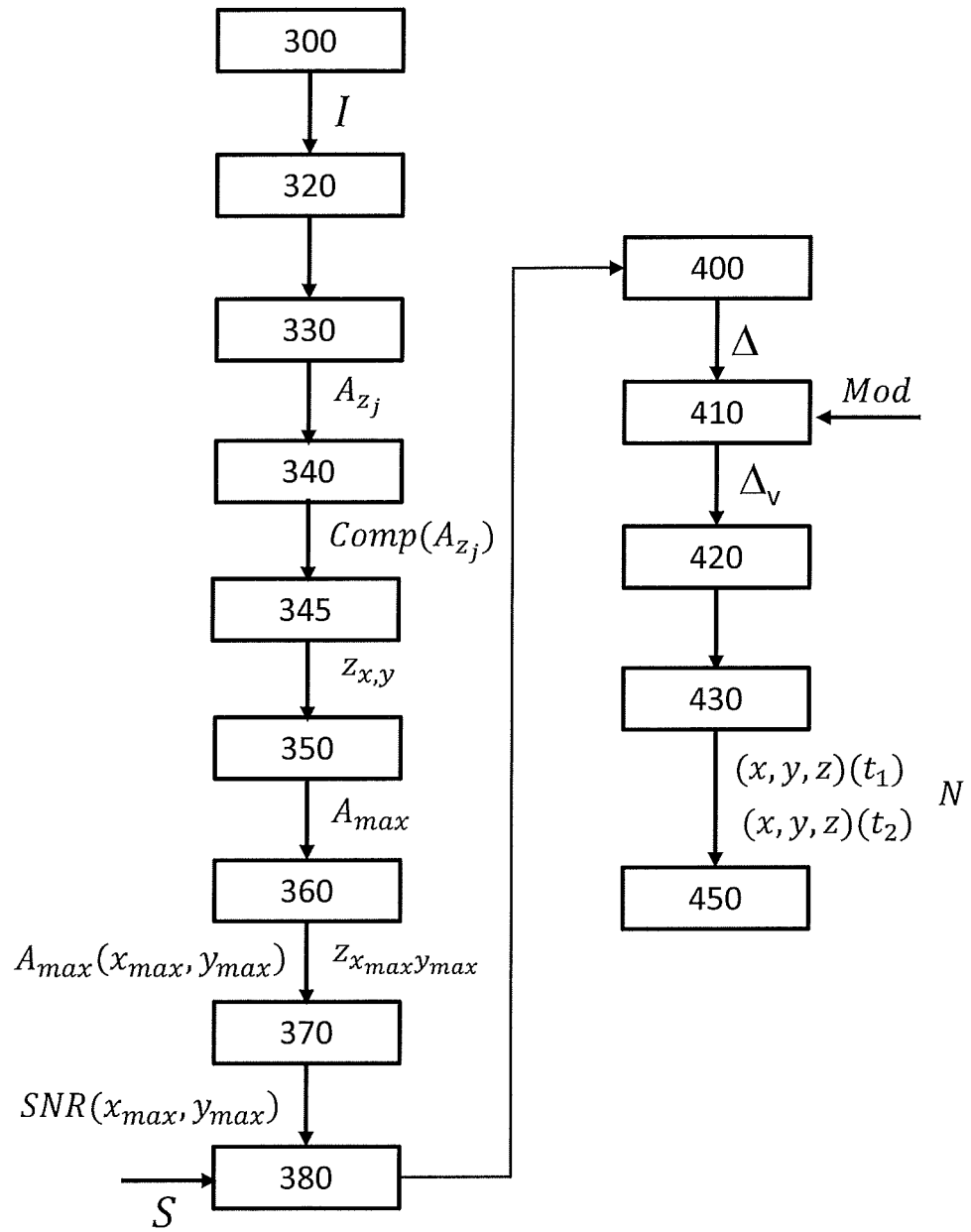
FIG. 4A illustrates a succession of steps allowing a second embodiment of the method to be implemented.

According to a second embodiment, the sample is illuminated with two pulses at a first time $t_1$ and at a second time $t_2$, respectively, and an image I the exposure time of which comprises the first time and the second time is acquired. Thus, in one and the same image, a signal representative of the positions of the particles at the first and second times is obtained. The steps of this embodiment are shown in FIG. 4A and described below:

Step 300: successively illuminating the sample at the first time and at the second time, and acquiring an image I, called the first image, through the first time and through the second time. The time interval between the two times may be very short, for example 5 ms.

Step 320: frequency filtering, analogously to step 120.

Step 330: propagating the filtered image, analogously to step 130, in order to obtain a stack of complex images.

Step 340: extracting a component of each complex image of the stack of complex images.

Step 345: digital focusing, analogously to step 145.

Step 350: forming a maxima image from the acquired image, analogously to step 150.

Step 360: searching for local maxima in the maxima image, analogously to step 160.

Step 370: taking into account the signal-to-noise ratio, analogously to step 170. This step allows a list of the radial coordinates ($x_{max}$, $y_{max}$) corresponding to a local maximum in the maxima image to be established, each pair of radial coordinates being associated with a transverse coordinate $z_{x_{max}, y_{max}}$. A list of three-dimensional positions ($x_{max}$, $y_{max}$, $z_{x_{max}, y_{max}}$) in the sample liable to include a particle is then obtained. With each three-dimensional position ($x_{max}$, $y_{max}$, $z_{x_{max}, y_{max}}$) is associated an estimation of the signal-to-noise ratio SNR($x_{max}$, $y_{max}$) of the image $I_{max}$ at the position ($x_{max}$, $y_{max}$). In contrast to the first embodiment, each of these three-dimensional positions is liable to be occupied by a particle 10a at the first time $t_1$ or at the second time $t_2$.

Step 380: thresholding depending on a signal-to-noise-ratio threshold, analogously to step 180. Only those three-dimensional positions the associated signal-to-noise ratio of which is higher than the threshold value are retained, the others being considered not to be representative of particles.

Figure 4B:
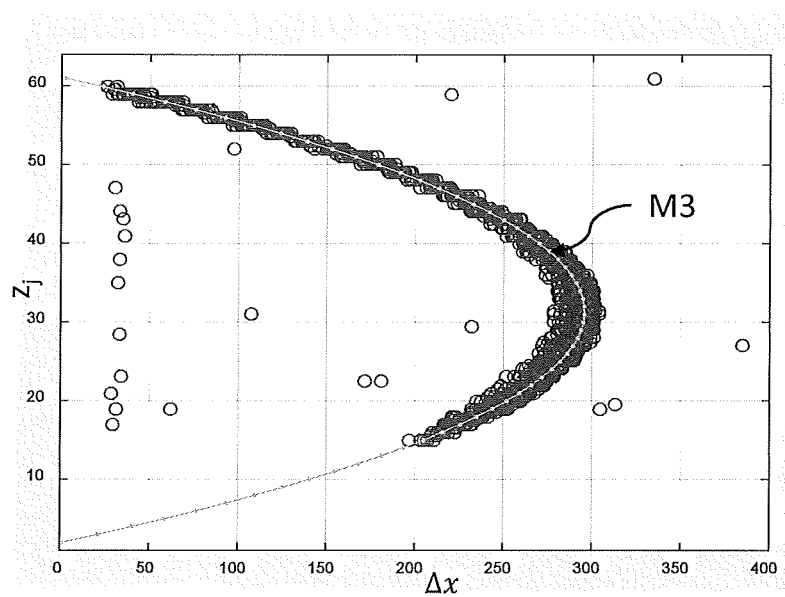
FIG. 4B shows the results obtained in a second experimental trial.

Step 400: Calculation of potential movements. In this step, potential movements Δ resulting from comparison of each three-dimensional position obtained in step 380 are determined. This results in a list of vectors of potential movements, the coordinates of which represent potential movements. FIG. 4B shows the potential movements obtained in a second experimental trial described below. This step may take into account a screening criterion based on a minimum movement, and therefore a minimum separation between two positions. Moreover, the screening criterion may also take into account the fact that the particles move, from A to B or from B to A, in a direction that is preset. For example, along the axis X, Δx is considered to be such that Δxmin≤Δx≤Δxmax, with Δxmin>0. This takes into account the fact that the three-dimensional positions of the acquired image are liable to correspond to positions of particles at the first time or at the second time.

Step 410: taking into account a movement model, analogously to step 210.

Step 420: validating movements, on the basis of a movement model, as described with respect to step 220. In FIG. 4B a movement model (curve M3) has been shown.

Step 430: defining the positions and/or number of particles corresponding to the movements validated in step 420.

According to this second embodiment, the method may include a step 450 of adjusting the signal-to-noise-ratio threshold used, similarly to the step 250 described above.

One advantage of this embodiment is to avoid recourse to image sensors having too high an acquisition frequency. For example, when the time interval between the first time and the second time is 5 ms, the first embodiment, based on an acquisition of two successive images, would require an acquisition rate of 200 images per second, this exceeding what is possible with usual image sensors. This embodiment is therefore suitable for particles having high speeds.

This embodiment was the subject of a second experimental trial, the particles being polystyrene beads of 2 µm diameter moving in air. FIG. 4B shows the movements and a modelled limit.

One limitation of this embodiment is that it takes into account only those particles present in the field of observation of the image sensor at the two times in question. The inventors have estimated that by applying a weighting factor to each detected movement, the counted number of particles is more reliable. The weighting factor for each movement $\Delta_k$ is determined using a probabilistic approach. The detection probability $p_k$ of coordinates $\Delta X_k$, $\Delta Y_k$ is such that:

$$p_k = \frac{(LX - |\Delta X_k|) \times (LY - |\Delta Y_k|)}{LX \times LY},$$

where LX and LY are the dimensions of the field observed by the detector 20 in the fluidic chamber 15, along the axis X and the axis Y, respectively.

If K is the number of movements $\Delta_k$ validated, each movement having for coordinates $\Delta X_k$ and $\Delta Y_k$, the number of particles in the fluidic chamber may be estimated by:

$$N = \Sigma_{k=1}^{k=K} \frac{1}{p_k} = \Sigma_{k=1}^{k=K} \frac{LX \times LY}{(LX - |\Delta X_k|) \times (LY - |\Delta Y_k|)}$$

This remains valid only if $|\Delta X_k|<LX$ or if $|Y_k|<LY$.

A variant that may be applied to each embodiment once the list of potential movements $\Delta$ has been established will now be described. This list is obtained at the end of step 200 of the first embodiment or of step 400 of the second embodiment. According to this variant, the particles flowing through the fluidic chamber are of various types, of different masses for example. Thus, each type of particle may have a movement, called a particulate movement, with respect to the fluid, that is specific thereto. The particulate movement may be induced by a property of the particle, on which the movement of the latter with respect to the fluid depends. The particle then moves in the fluid under the effect of a force that is dependent on said property, for example under the effect of a field to which the particle is subjected. It may for example be a question of an electric or magnetic field, in which case a particle is subjected to a force depending on its charge. It may also be a question of a gravitational field, in which case the particle moves with respect to the fluid depending on its mass. Thus, it is possible to define a particulate movement model for the movement of the particles with respect to the fluid, one parameter of which is said property of the particle. The particulate movement of each particle is preferably oriented with an orientation nonparallel to the flow direction of the fluid, but this condition is not essential. It is optimal for the particulate movement to be perpendicular to the flow direction of the fluid. By applying the particulate movement model to the previously validated three-dimensional movements $\Delta$, it is possible to determine the particle property forming a parameter of the particulate movement model. It is then possible to classify the particles depending on their property and to count the particles as a function of a value of said property.

It is possible for example to take into account a particulate movement model corresponding to a preset value of the property. Next, for each particle, a deviation $\varepsilon$ from this model is determined. It is then possible to classify the particles depending on the deviation $\varepsilon$, from the particulate movement model, that has been attributed thereto. The particles are then classified depending on their particulate movement. Particles for which the deviation is zero have a property corresponding to the preset value. The property of the other particles depends on the deviation calculated for each thereof.

A third experimental trial was carried out in order to implement this variant, using polystyrene beads of 1 μm diameter and of 2 μm diameter. The fluidic chamber was maintained placed such that the particles were entrained by airflowing horizontally, the flow axis X being horizontal. The experimental device is shown in FIG. 1A, the XZ plane being a horizontal plane. The particles were entrained horizontally by the carrier fluid, in the present case air, along the horizontal axis. They experienced the effects of gravity, along a vertical axis Y, perpendicular to the flow axis. The dimensions of the fluidic chamber 15 were 10 mm and 20 mm along the axes Z and Y, respectively. The fluidic chamber had, in a YZ plane, a rectangular cross section of dimensions of 9.6 mm×20 mm.

It may be shown that if $\Delta t=t_2-t_1$, a variation in the movement $\Delta Y$ along the axis Y is such that $\Delta Y=K(\rho_b d_b^2 - \rho_a d_a^2)\Delta t$, where:

$\rho_b$: density of the second type of particles;
$d_b$: diameter of the second type of particles;
$\rho_a$: density of the first type of particles;
$d_a$: diameter of the first type of particles; and
K is a constant equal to 34.7.

In this example, the considered property of each particle is its aerodynamic diameter, corresponding to the product of the diameter of a particle multiplied by the square root of its density.

For an acquisition frequency of 10 Hz or of 4 Hz, $\Delta Y$ is equal to 12.4 and 31 μm, i.e. 5.6 and 14.1 pixels, for the first type and second type of particle, respectively.

In each reconstructed image, the particles of 2 μm diameter appear more dearly than particles of 1 μm diameter: thus, the signal-to-noise ratio corresponding to the particles of large diameter is higher than the signal-to-noise ratio corresponding to the particles of small diameter.

When the potential movements $\Delta$ are established (step 200), a movement is considered to be a potential movement when the signal-to-noise ratios associated with the two positions, defining the movement, are similar. A signal-to-noise ratio $S_\Delta$ may then be assigned to each movement $\Delta$, this ratio being obtained by averaging the signal-to-noise ratios respectively associated with each position forming the movement. The signal-to-noise ratio $S_\Delta$ of the movements of the first type of particle (particles of 1 μm diameter) is lower than the signal-to-noise ratio of the movements of the second type of particle (particles of 2 μm diameter). Moreover, the movement, along the vertical axis Y, of the first type of particle is smaller than the movement, along the same axis, of the second type particle.

The particulate movement modelled for the second type of particle is subtracted from each determined movement $\Delta Y$ along the axis Y.

Figure 5:
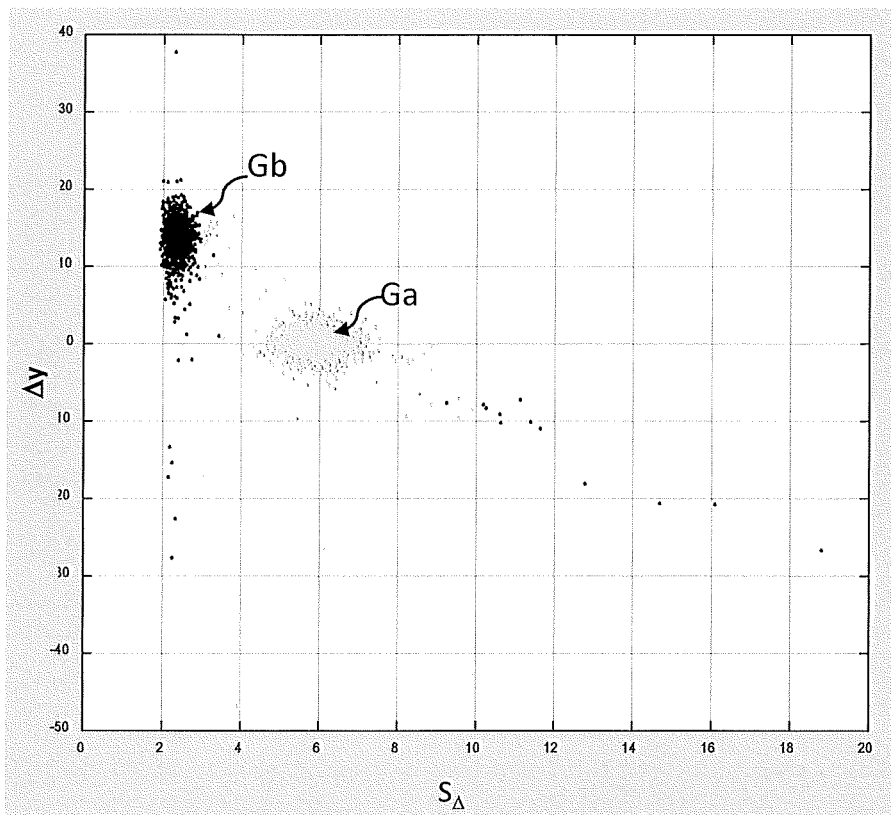
FIG. 5 shows the results obtained in a third experimental trial, implementing a variant of the invention.

FIG. 5 shows the movements $\Delta Y$ of each particle after the particulate movement model has been subtracted, as a function of the signal-to-noise ratio attributed to each movement. The acquisition frequency is 10 Hz. Each point in FIG. 5 represents a validated movement. A segmentation of the movements is observed:

movements corresponding to the second type of particle are grouped in a group Gb centered on the coordinate $\Delta Y=12.5$ μm;

movements corresponding to the first type of particle are grouped in a group Ga, lying about the coordinate $\Delta Y=0$.

It may also be seen that the movements associated with the first type of particle have a signal-to-noise ratio $S_\Delta$ lower than the movements associated with the second type of particle.

This variant allows particles to be counted depending on a property, such as mass, charge, or aerodynamic diameter. It may also be employed to discriminate between bacteria, depending on their motility. It is thus possible to discriminate between bacteria of *Staphylococcus* type (nonmotile, follow the fluid) and bacteria of *E. coli* type (motile, move with respect to the fluid).

In the embodiments described above, the images are acquired with an image sensor 20 placed in a lensless imaging configuration, no image-forming optics being placed between the image sensor in the fluidic chamber. Specifically, such a device allows three-dimensional positions of particles to be determined using a two-dimensional image sensor and inexpensive instrumentation. Such a device is therefore therefore particularly suitable for implementing the invention. However, the invention applies to other imaging configurations allowing positions, and in particular three-dimensional positions, of particles at two successive times to be obtained. The embodiments described above apply to a defocused image sensor forming a defocused image of the sample using the known digital-holography-microscopy technique. The advantage is to be able to observe particles of small size, at the detriment of a small field of observation. It is also possible to obtain the three-dimensional positions of particles via other imaging techniques, implementing a plurality of image sensors. These sensors may for example lie parallel to one another, the three-dimensional position of the particles being obtained via stereo vision. Two sensors lying in different planes, for example perpendicular to each other, are also envisionable.

The invention may be applied to the detection of solid particles, for example pollutants or dusts, in air, but also to the detection of particles, in particular biological particles, in a liquid. It may also be applied in applications associated with the monitoring of fluids, in industrial, environmental, health or food-processing industries fields.

The invention claimed is:

1. A method for counting particles moving in a fluid flowing through a fluidic chamber, the method comprising:
    a) placing the fluidic chamber between a light source and an image sensor, the image sensor lying in a detection plane;
    b) illuminating the fluidic chamber with the light source, the light source emitting an incident light wave that propagates along a propagation axis, and acquiring, with the image sensor, a first image representative of an exposure wave to which the image sensor is exposed, the image sensor including various pixels, each pixel being associated with a radial coordinate in the detection plane;
    c) on the basis of the acquired first image, obtaining three-dimensional coordinates of particles, in the fluidic chamber, at a first time;
    d) obtaining three-dimensional coordinates of particles in the fluidic chamber at a second time, subsequent to the first time;
    e) on the basis of the coordinates of the particles obtained at the first time and at the second time, determining potential movements of the particles between said times;
    f) acquiring a model of the movement of the fluid in the fluidic chamber;
    g) on the basis of the model of the movement of the fluid acquired in step f), validating movements among the potential movements calculated in step e); and
    h) on the basis of the movements validated in step g), determining a number of particles and/or coordinates of the particles at the first time and/or at the second time, wherein step c) comprises
        ci) obtaining a first image of interest from the first image acquired in step b), and applying a digital propagation operator to the first image of interest in order to propagate the first image of interest, b a plurality of reconstruction distances, along the propagation axis, so as to obtain a first stack of images, including as many reconstructed complex images as there are reconstruction distances, each reconstructed complex image being representative of the exposure wave to which the image sensor is exposed;
        cii) for at least one radial coordinate defined in the first image of interest, determining a reconstruction distance that maximizes variation in a component of each reconstructed complex image forming the first stack of images, along an axis parallel to the propagation axis and passing through said radial coordinate, the determined reconstruction distance forming a transverse coordinate associated with said radial coordinate, a value of the component calculated at the reconstruction distance being a maximum value associated with said radial coordinate, substep cii) being carried out for all or some radial coordinates associated with pixels of the first image of interest;
        ciii) establishing a list of three-dimensional positions, each three-dimensional position including a radial coordinate and the associated transverse coordinate determined in substep cii), each three-dimensional position being associated with the maximum value obtained in substep cii); and
        civ) selecting three-dimensional positions depending on the associated maximum values.

2. The method of claim 1, wherein step c) comprises:
    on the basis of each reconstructed complex image, obtaining radial coordinates of particles in the fluidic chamber at the first time.

3. The method of claim 1, wherein the first image of interest is:
    the first image acquired in step b);
    or the first image acquired in step b), from which an image of the fluidic chamber is subtracted, the image of the fluidic chamber is acquired by the image sensor, prior or subsequently to the acquisition of the first image, the subtraction being weighted by a weighting term;
    or the first image acquired in step b), from which an average of images acquired prior and subsequently to the acquisition of the first image is subtracted.

4. The method of claim 1, wherein, in substep cii), the component includes a real part, or an imaginary part, or a modulus, or a phase of each reconstructed complex image forming the first stack of images.

5. The method of claim 1, wherein substep civ) comprises:
    forming a first maxima image, each pixel of the first maxima image is associated with a three-dimensional position determined in substep ciii) and is assigned the maximum value determined, in substep ciii), for said three-dimensional position;
    selecting, in the first maxima image, pixels having values that are maximum in a neighbouring zone defined around each pixel; and
    calculating, for each selected pixel, a signal-to-noise ratio depending on the maximum value and the values of pixels of the first maxima image located in a calculation zone lying around said selected pixel;
    such that each three-dimensional position is selected depending on the signal-to-noise ratio calculated for the selected pixels of the first maxima image.

6. The method of claim 1, wherein step d) includes acquiring, with the image sensor, a second image, each pixel of the second image is associated with a radial coordinate in the detection plane.

7. The method of claim 6, wherein step d) comprises:
    di) obtaining a second image of interest from the acquired second image and applying a digital propagation operator to the second image of interest in order to propagate the second image of interest, by a plurality of reconstruction distances, along the propagation axis, so as to obtain a second stack of images, including as many reconstructed complex images as there are reconstruction distances, each reconstructed complex image being representative of an exposure wave to which the image sensor is exposed at the second time;

dii) for at least one radial coordinate defined in the second image of interest, determining a reconstruction distance that maximizes variation in a component of each reconstructed complex image forming the second stack of images; along an axis parallel to the propagation axis and passing through said radial coordinate, the determined reconstruction distance forming a transverse coordinate associated with said radial coordinate, a value of the component calculated at said reconstruction distance being a maximum value associated with the radial coordinate, substep dii) being carried out for all or some radial coordinates associated with pixels of the second image of interest;

diii) establishing a list of three-dimensional positions, each three-dimensional position including a radial coordinate and the associated transverse coordinate determined in substep dii), each three-dimensional position being associated with the maximum value obtained in substep dii); and div) selecting three-dimensional positions depending on the associated maximum values.

8. The method of claim 7, wherein, in substep di), the second image of interest is:
the acquired second image;
or the acquired second image, from which an image of the fluidic chamber is subtracted, the image of the fluidic chamber acquired by the image sensor, prior or subsequently to the acquisition of the second image, the subtraction being weighted by a weighting term between 0 and 1;
or the acquired second image; from which an average of images acquired prior and subsequently to the acquisition of the second image is subtracted.

9. The method of claim 4; wherein, in substep dii), the component includes a real part, or an imaginary part, or a modulus, or a phase of each reconstructed complex image forming the second stack of images.

10. The method of claim 7, wherein substep div) includes:
forming a second maxima image, each pixel of the second maxima image is associated with a three-dimensional position determined in substep diii) and is assigned the maximum value determined, in substep diii), for the three-dimensional position;
selecting, in the second maxima image, pixels having values that are maximum in a neighbouring zone defined around each pixel; and
calculating, for each selected pixel, a signal-to-noise ratio depending on the maximum value and the values of pixels of the second maxima image located in a calculation zone lying around said selected pixel;
such that each three-dimensional position is selected depending on the signal-to-noise ratio calculated for the selected pixels of the second maxima image.

11. The method of claim 1, wherein:
step b) includes two successive illuminations of the fluidic chamber with the light source, at the first time and at the second time, such that the first image represents the exposure wave at each of the first time and the second time; and
steps c) and d) comprise obtaining coordinates of particles at the first time and at the second time.

12. The method of claim 1, wherein step e) includes comparing the coordinates of particles in the fluidic chamber determined at the first time and at the second time, establishing a list of potential movements of the particles between the first time and the second time.

13. The method of claim 1, herein step g) includes determining a movement range using the model of the movement acquired in step f), the potential movements being validated when they are comprised in said movement range.

14. The method of claim 1, wherein step g) includes subtracting, from each potential movement, a movement according to the model of the movement.

15. The method of claim 1, wherein:
the fluid includes particles, each particle having a property and moving, with respect to the fluid, according to a particulate movement model; and
the particulate movement model depends on said property of the particles,
the method including, on the basis of movements validated in step g), a step i) of using at least one particulate movement model to count the particles depending on a value of the property.

16. The method of claim 15, wherein the property is a mass, or an electric charge, or an aptitude to move in the fluid.

17. The method of claim 15, including:
acquiring a particulate movement model for a preset value of the property; and
calculating discrepancies in the movements of each particle with respect to said particulate movement model for the present value of the property;
such that the property of each particle is deter fined depending on said discrepancies and said preset value of the property.

18. The method of claim 15, wherein the fluid flows in a flow direction, and wherein the particulate movement occurs in another direction non-parallel to said flow direction.

19. A device for counting particles flowing through a fluidic chamber, the device comprising:
a light source configured to illuminate the fluidic chamber; and
an image sensor lying in a detection plane, the fluidic chamber being interposed between the image sensor and the light source, the image sensor being configured to acquire at least one image of the fluidic chamber illuminated by the light source,
the device including a processor configured to implement steps c) to h) of the method according to claim 1 on the basis of at least one image acquired by the image sensor.

* * * * *